Feb. 7, 1961 O. O. DUNHAM Plant Pat. 2,023
CHRYSANTHEMUM PLANT
Filed Sept. 16, 1959
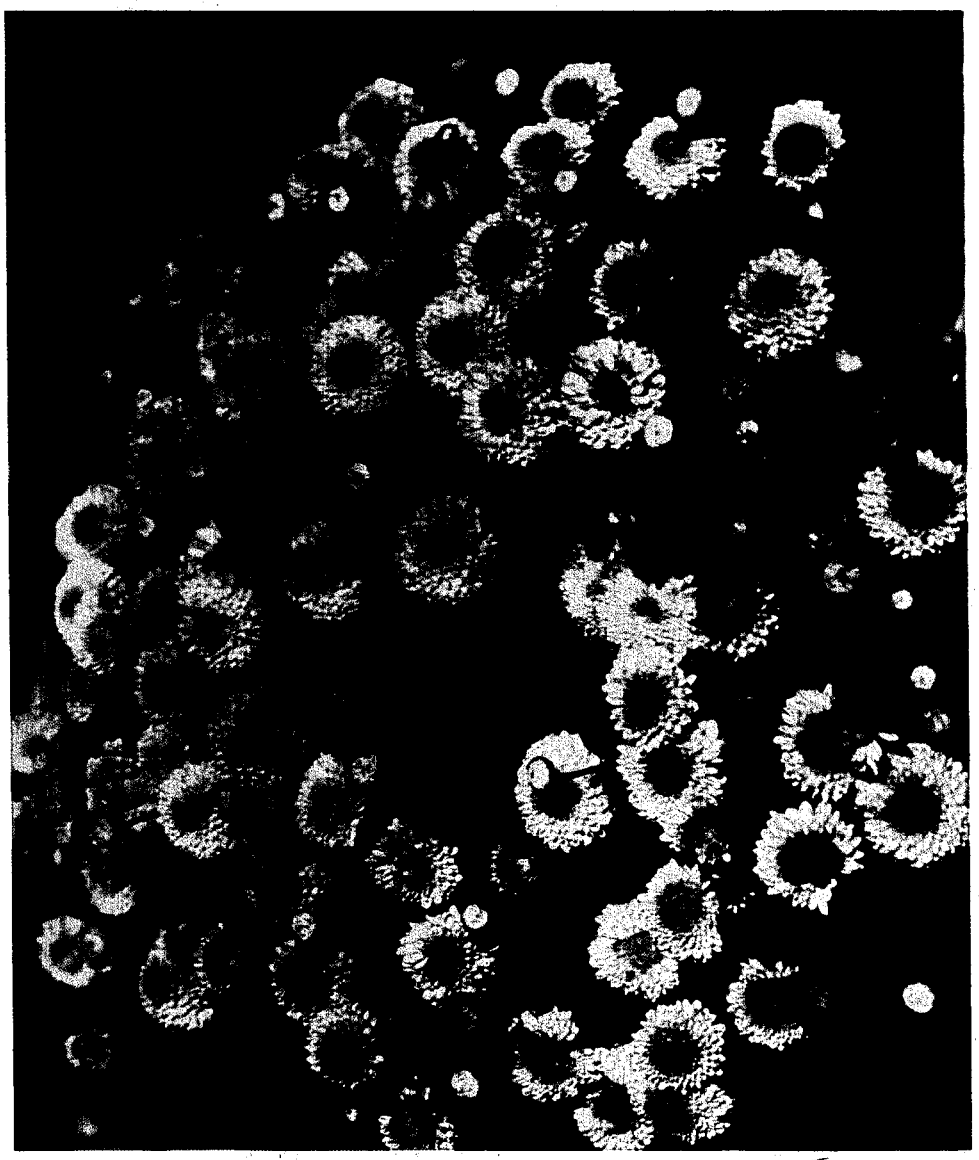
Inventor
O. O. Dunham
by Robb & Robb
Attorneys United States Patent Office Plant Pat. 2,023
Patented Feb. 7, 1961

2,023

CHRYSANTHEMUM PLANT

Orville O. Dunham, Rte. 4, Niles, Mich.

Filed Sept. 16, 1959, Ser. No. 840,483

1 Claim. (Cl. 47—60)

My present invention comprises a new and distinct variety of chrysanthemum plant which is the result of crossing the variety "Little Dorrit" an unpatented variety, with a variety of my own introduction, likewise unpatented and which I designate as seedling Number 53136.

The object of this invention has been to produce a new variety of chrysanthemum plant of the *indicum* type which derives the color of its blooms from both parents, a darker color from one, and a lighter color from the other, but which will constitute an improvement over either of the parents with better shape, bloom and additionally provide early and continuous blooming habits.

For a period of time I have been conducting an intensive program of development, and this present new variety is one of the results thereof, which has required the careful selection and cross-breeding of various plants, basically those of the American garden chrysanthemum type, so-called with the plants of the type known as the English early chrysanthemum. In conducting this program I have endeavored to take advantage of the continuous flowering features of the English early chrysanthemum with the early flowering feature of the American garden chrysanthemum and some of the attributes of the latter relating to the continuous nature of its bloom.

The result of the specific hybridization previously referred to has been to produce my present new and distinct variety of chrysanthemum plant characterized by the strong reddish purple to light purplish pink color of its blooms, the small honeycomb-like globular form thereof, the compact shape of the plant, and its better, early, continuous and long blooming habit.

More specifically, the blooms of my new variety are of the strong reddish purple to light purplish pink color (Nickerson Color Fan published by the Munsell Company), the blooms having the lighter outer color with a darker center. As grown in the vicinity of Niles, Michigan, in uniform culture, plants of my new variety have grown to an average height of 12 to 16".

My new variety derives a number of characteristics from both parents, but better characteristics than either separately and my new variety differs from both of its parents and from other known varieties in many respects.

In comparing the color of my new variety with the color of the blooms of the variety "Little Dorrit," I note that the color of the latter has apparently been transmitted to the seedling hereof so as to provide a lighter outer portion of the bloom whereas the inner or center portion of the bloom appears to have derived its color from the parent seedling Number 53136. The petal arrangement in my new variety is similar to the parent Number 53136 but the blooms are more uniform, and globular than those of the variety "Little Dorrit." The petal arrangement of my new variety is very double and innumerable petals are found under normal conditions.

Under the conditions of culture previously mentioned, which have been undertaken in the region of Niles, Michigan, plants of my new variety have grown very vigorously, in somewhat more compact form, branching and slightly more dwarfed than the parent seedling Number 53136.

My new variety when grown in the region of Niles, Michigan, blooms from early September continuously until a killing frost, the blooms being small in size and in clusters with profuse numbers of blooms on each plant.

The earliness and continuous blooming habit and dwarfed, compact shape derives from the pollen parent, seedling Number 53136, and small honeycomb-like globular blooms are superior to those of the seed parent "Little Dorrit."

My new variety has been asexually reproduced by cuttings in the vicinity of Niles, Michigan.

My new variety has been found to have retained its distinctive characteristics through successive asexual reproduction.

The accompanying drawing forming a part hereof shows a typical plant of my new variety of chrysanthemum plant.

The following is a detailed description of my new variety of chrysanthemum plant, the color references being to the Nickerson Color Fan published by the Munsell Color Company:

*Description form*

Parentage: Seedling.

*Seed parent.*—"Little Dorrit" (English origin—unpatented).

*Pollen parent.*—#53136 (unpatented) (my own seedling).

Classification: Botanic *Chrysanthemum indicum.*

*Flower*

Blooming habit: Blooms profusely and continuously from early in September until a killing frost. Observations were made in the vicinity of Niles, Michigan, during September.

Bud:

*Size.*—Small.

*Form.*—Short with flat top. Not affected materially by hot or wet weather.

Color:

*When petals begin to unfurl.*—7.5RP 5/12.

*When half blown.*—Inside of petals—7.5RP 6/12. Reverse of petals—5RP 8/5.

*Sepals.*—Of no consequence.

*Calyx.*—Shape—funnel. Size—small. Aspect—hairy.

*Peduncle.* — Length — medium. Aspect—rough, hairy. Strength—stiff, erect. Bud opens well and is not affected by adverse conditions.

Bloom:

*Size.*—Small. Average size when fully expanded 1–1½".

*Borne.*—In clusters, pyramidal and irregular.

*Stems.*—Short, strong.

*Form.*—When first open—globular. Permanence—retains its form to the end.

*Petalage.*—Very double, Number of petals under normal conditions—innumerable.

*Color.*—Center of flower—7.5RP 4/11 washed with 7.5RP 6/12. Outer petals—2.5RP 6/10 washed with 2.5RP 8/5. Base of petals (singlet)—2.5RP 6/10. Inside of petals—2.5RP 6/10. Reverse of petals—2.5RP 9/2. General tonality from a distance—2.5RP 5/10 washed with 2.5RP 8/5.

*Discoloration.*—General tonality at end of: First week—retains same color. Second week—slightly lighter over all. Third week—slightly lighter over all.

Petals:

*Texture.*—Thin. Not affected by wet or hot weather.

*Appearance.*—Inside—velvety. Outside—satiny.

*Form.*—Oval.

*Arrangement.*—Imbricated.

*Persistence.*—Hang on and dry.

*Lastingness.*—On the plant—very long. Cut flower—very long.

*Genital organs*

Stamens, anthers: Small, few.

*Color.*—10Y 9/9 brilliant greenish yellow.

*Arrangement.*—Regular around styles.

Stamens, filaments: Medium. Color—white.

Pollen: 2.5GY 9/8 brilliant yellow green.

Styles: Columnar.

Stigmas: Color—white.

Ovaries: All enclosed in calyx.

*Plant*

Form: Bush.

Growth: Vigorous, dwarf, branching, compact.

Foliage:

*Size.*—Small.

*Quantity.*—Normal.

*Shape.*—3 lobed.

*Texture.*—Upper side—velvety. Under side—velvety. Ribs and veins—ordinary.

*Edge.*—Smooth.

I claim:

A new and distinct variety of chrysanthemum plant substantially as herein disclosed, characterized as to novelty by strong reddish purple to light purplish pink color of its blooms, the small honeycomb-like globular form thereof, the compact shape of the plant, and its better, early, continuous and long blooming habit.

No references cited.